United States Patent [19]

Cuca et al.

[11] Patent Number: 5,494,681
[45] Date of Patent: Feb. 27, 1996

[54] TASTEMASKED PHARMACEUTICAL MATERIALS

[75] Inventors: Robert C. Cuca, Edwardsville, Ill.; Ronald S. Harland, Chesterfield, Mo.; Thomas C. Riley, Jr., Manchester, Mo.; Yury Lagoviyer, St. Louis, Mo.; R. Saul Levinson, Chesterfield, Mo.

[73] Assignee: KV Pharmaceutical Company, St. Louis, Mo.

[21] Appl. No.: 288,849

[22] Filed: Aug. 11, 1994

Related U.S. Application Data

[63] Continuation of Ser. No. 982,971, Nov. 30, 1992, abandoned.

[51] Int. Cl.⁶ ............................................. A61K 9/14
[52] U.S. Cl. ........................ 424/484; 424/489; 424/495; 424/494; 424/502
[58] Field of Search ............................ 424/484, 489, 424/490, 491

[56] References Cited

U.S. PATENT DOCUMENTS

| | | | |
|---|---|---|---|
| 2,954,322 | 9/1960 | Heilig et al. | 424/481 |
| 3,133,863 | 5/1964 | Tansey | 424/465 |
| 3,420,931 | 1/1969 | Daum et al. | 424/479 |
| 3,458,622 | 7/1969 | Hill | 424/468 |
| 3,806,603 | 4/1974 | Gaunt et al. | 514/783 |
| 3,860,733 | 1/1975 | Morse et al. | 426/302 |
| 3,879,511 | 4/1975 | Goodhart et al. | 424/495 |
| 3,950,508 | 4/1976 | Mony et al. | 424/465 |
| 4,117,801 | 10/1978 | Dannelly et al. | 118/20 |
| 4,140,756 | 2/1979 | Gallian | 424/21 |
| 4,252,786 | 2/1981 | Weiss et al. | 424/495 |
| 4,415,547 | 11/1983 | Yu et al. | 424/469 |
| 4,590,075 | 5/1986 | Wei et al. | 426/5 |
| 4,597,970 | 7/1986 | Sharma et al. | 426/5 |
| 4,716,041 | 12/1987 | Kjornaes et al. | 424/468 |
| 4,747,881 | 5/1988 | Shaw et al. | 424/476 |
| 4,790,991 | 12/1988 | Shaw et al. | 424/441 |
| 4,800,087 | 1/1989 | Mehta | 424/497 |
| 4,806,603 | 2/1989 | Hess et al. | 525/445 |
| 4,810,501 | 3/1989 | Ghebre-Sallassie | 424/469 |
| 4,816,265 | 3/1989 | Cherukuri et al. | 426/5 |
| 4,818,539 | 4/1989 | Shaw et al. | 424/441 |
| 4,843,098 | 6/1989 | Shaw et al. | 424/476 |
| 4,851,226 | 7/1989 | Julian et al. | 424/441 |
| 4,851,392 | 7/1989 | Shaw et al. | 424/441 |
| 4,865,851 | 9/1989 | James et al. | 424/498 |
| 4,916,161 | 4/1990 | Patell | 514/570 |
| 4,925,674 | 5/1990 | Giannini et al. | 424/469 |
| 4,931,293 | 6/1990 | Cherukuri et al. | 426/5 |
| 4,933,190 | 6/1990 | Cherukuri et al. | 426/5 |
| 4,946,685 | 8/1990 | Edgren et al. | 424/472 |
| 4,966,770 | 10/1990 | Giannini et al. | 424/461 |
| 4,981,698 | 1/1991 | Cherukuri et al. | 348/415 |
| 5,004,595 | 4/1991 | Cherukuri et al. | 424/48 |
| 5,013,557 | 5/1991 | Tai | 424/493 |
| 5,026,560 | 6/1991 | Makino et al. | 424/494 |
| 5,057,319 | 10/1991 | Gottwald et al. | 424/441 |
| 5,059,416 | 10/1991 | Cherukuri et al. | 424/48 |
| 5,075,114 | 12/1991 | Roche | 424/470 |
| 5,082,669 | 1/1992 | Shirai et al. | 424/495 |
| 5,084,278 | 1/1992 | Mehta | 424/441 |
| 5,085,868 | 2/1992 | Mattsson et al. | 424/490 |
| 5,098,714 | 3/1992 | Wright et al. | 424/423 |

FOREIGN PATENT DOCUMENTS

| | | |
|---|---|---|
| WO92/12704 | 8/1992 | European Pat. Off. . |
| 1462193 | 12/1966 | France . |

*Primary Examiner*—Thurman K. Page
*Assistant Examiner*—William E. Benston, Jr.
*Attorney, Agent, or Firm*—Nath & Associates; Gary M. Nath; Suet M. Chong

[57] ABSTRACT

A substantially tasteless pharmaceutical delivery system, which comprises a) an active material; and b) a spatially oriented matrix comprising (i) a wax core material having a melting point within the range of about 50° C. and about 200° C.; and (ii) a regional hydrophobic polymer material and method for making the same.

14 Claims, No Drawings

5,494,681

TASTEMASKED PHARMACEUTICAL MATERIALS

This application is a continuation application of U.S. patent application Ser. No. 07/982,971, filed Nov. 30, 1992, abandoned, the entire contents of which are hereby incorporated in their entirety.

BACKGROUND OF THE INVENTION

1. Field of the Invention

This invention relates to tastemasked pharmaceutical materials and to methods for making the same. More particularly, the invention relates to tastemasking the noxious, bitter tastes associated with bad tasting drugs using a spatially oriented hydrophobic matrix material to prepare pleasant tasting compositions.

2. Description of the Prior Art

Oral pharmaceutical formulations are administered to patients in many forms, such as liquid solutions, emulsions, or suspensions, as well as in solid form such as capsules or tablets. Preparations administered in tablet or capsule form are usually intended to be swallowed whole. Therefore, the often disagreeable taste of the active ingredient need not be taken into account in formulating the medicine, except as a means to prevent the taste from being apparent during the short time that the medicine is in the mouth. Such means may include forming the active into a matrix preparation; the use of capsules or simply compressing a tablet firmly so that it will not begin to disintegrate during the short time that it is intended to be in the mouth. In some preparations, the unpleasant tasting particles are coated with water-soluble and/or water-insoluble coating agents, film forming polymers, water-swelling agents and acid soluble agents. Some of these procedures are described in the following patents.

U.S. Pat. No. 2,954,322 to Heilig et al, discloses a tablet intended for oral administration wherein the whole tablet is coated with a mixture of shellac and polyvinylpyrrolidone. It is intended that the tablet be swallowed whole and that the coating will disintegrate in the stomach to release the active medicament.

U.S. Pat. No. 3,133,863 to Tansey et al, discloses a method for forming granules of medicament that can be compressed into tablet form, wherein the granules include various polymers dispersed throughout the granules. One embodiment comprises acetaminophen mixed with PVP and methyl cellulose.

U.S. Pat. No. 3,420,931 to Daum et al, discloses sugar-coated pharmaceutical preparations ("dragees") coated with a mixture of sugar and a vinyl polymer such as PVP. The coating may also contain cellulose derivatives. The reference specifically discloses cellulose derivatives such as methyl cellulose, ethyl cellulose, carboxymethyl cellulose, hydroxyethyl cellulose, and hydroxypropyl cellulose.

U.S. Pat. No. 3,458,622 to Hill discloses a controlled release tablet wherein the active medicament is contained in a core comprising a matrix of a mixture of PVP and a carboxyvinyl(polyacrylic acid)hydrophilic polymer.

U.S. Pat. No. 4,252,786 to Weiss et al, discloses a controlled release tablet similar to that of Hill, wherein the core containing the active medicament is coated with a relatively insoluble, water permeable, rupturable film comprising a combination of hydrophobic and hydrophilic polymers. Cellulose acetate is disclosed as one of the hydrophobic polymers. The tablets of Weiss et al. and Hill are intended to be swallowed whole.

U.S. Pat. No. 4,415,547 to Yu et al, discloses sustained release pharmaceutical tablets consisting essentially of drug pellets encapsulated with a water soluble film-forming substance and a water-insoluble film-forming substance. The materials are blended and compressed into tablet form with a compressible tableting mixture.

U.S. Pat. No. 5,059,416 to Cherukuri et al, discloses a process for preparing a zinc compound delivery system comprised of a zinc core material coated with a first hydrophilic coating comprising a hydrocolloid material and a second hydrophobic coating selected from the group consisting of fats, waxes and mixtures thereof. The delivery system masks the bitter flavor characteristic of zinc compounds.

U.S. Pat. No. 4,597,970 to Sharma et al, discloses a delivery system capable of effecting a controlled release of core material comprising: (A) at least one natural or artificial sweet material; and (B) a hydrophobic matrix consisting essentially of (i) lecithin; and (ii) an edible material having a melting point in the range of about 25° C. to about 100° C. selected from the group consisting of (a) fatty acids having an iodine value of about 1 to about 10, (b) natural waxes, (c) synthetic waxes and (d) mixtures thereof; and (iii) at least one glyceride.

Unlike the prior art, the present invention is directed to the discovery of a matrix system that can be used to coat the active component and which achieves a good balance between tastemasking and control of bioavailability of both water-soluble and insoluble active components.

SUMMARY OF THE INVENTION

This invention relates to a substantially tasteless pharmaceutical delivery system, comprising: (a) an active material and (b) a spatially oriented matrix comprising (i) a major amount of a wax core material having a melting point within the range of about 50° C. and about 200° C.; and (ii) a minor amount of a hydrophobic polymer material.

An alternative embodiment involves use of an active material which is a drug selected from the group consisting of analgesics, anti-inflammatories, antihistamines, antitussives, expectorants, decongestants, narcotics, antibiotics, bronchodilators, cardiovasculars, central nervous system drugs, minerals, vitamins, metal salts, and mixtures thereof disbursed within a matrix comprising a wax core material and a hydrophobic polymer material.

A further embodiment of the invention involves a process for preparing a substantially tasteless pharmaceutical delivery system, comprising melting and blending a major amount of a wax core material and a minor amount of a hydrophobic polymer material at a temperature from about 50° C. to about 200° C. to form a matrix; blending the matrix to form a homogenous mixture of components; adding the active material to the matrix, wherein the temperature of the matrix is maintained below the decomposition temperature of the active material; uniformly dispersing the active material within the matrix to obtain of smooth suspension; and solidifying the mass to form particles of the substantially tasteless pharmaceutical delivery system.

DETAILED DESCRIPTION OF THE INVENTION

The present invention involves the preparation of a tastemasked system by casting or spin congealing melt dispersions and/or solutions of drug or other active material in a molten blend of materials. In this manner a substantially tasteless pharmaceutical delivery system is formed which comprises: (a) an active material; and (b) a spatially oriented matrix comprising (i) a major amount of wax core material having a melting point within the range of about 50° C. and about 200° C.; and (ii) a minor amount of a hydrophobic polymer material.

The active(s) or drug(s) may be described as a single drug entity or a combination of entities. A drug with high water-solubility is expected to produce immediate release systems, whereas a drug with low water-solubility may produce a controlled or delayed release system. However, controlled or delayed release systems may result when using drugs with high water-solubility. The term "drug" includes without limitations, medicaments, vitamins, mineral supplements and other chemical or biological substances intended for use in the treatment prevention, diagnosis, cure or mitigation of disease or illness, or substances which affect the structure or function of the body.

Suitable categories of drugs that may be employed in the instant aggregate may vary widely and generally represent any stable drug combination. Illustrative categories and specific examples include: (a) antitussives, such as dextromethorphan, dextromethorphan hydrobromide, noscapine, carbetapentane citrate, and chlophedianol hydrochloride; (b) antihistamines, such as chlorpheniramine maleate, phenindamine tartrate, pyrilamine maleate, doxylamine succinate, and phenyltoloxamine citrate; (c) decongestants, such as phenylephrine hydrochloride, phenylpropanolamine hydrochloride, pseudoephedrine hydrochloride, ephedrine; (d) various alkaloids, such as codeine phosphate, codeine sulfate and morphine; (e) mineral supplements such as potassium chloride, zinc chloride and calcium carbonates, magnesium oxide and other alkali metal and alkaline earth metal salts; (f) laxatives, vitamins and antacids; (g) ion exchange resins such as cholestyramine; (h) anti-cholesterolemic and anti-lipid agents; (i) antiarrhythmics such as N-acetylprocainamide; (j) antipyretics and analgesics such as acetaminophen, aspirin and ibuprofen; (k) appetite suppressants such as phenylpropanolamine hydrochloride or caffeine; and (1) expectorants such as guaifenesin.

Additional useful active medicaments include anti-inflammatory substances, coronary dilators, cerebral dilators, peripheral vasodialators, anti-infectives, psychotropics, antimanics, stimulants, laxatives, gastro-intestinal sedatives, antidiarrheal preparations, anti-anginal drugs, vasodialators, anti-arrythmics, antihypertensive drugs, vasoconstrictors and migraine treatments, antibiotics, tranquilizers, anti-psychotics, antitumor drugs, anticoagulants and antithrombotic drugs, hypnotics, sedatives, anti-emetics, anti-nauseants, anticonvulsants, neuromuscular drugs, hyper- and hypoglycaemic agents, thyroid and antithyroid preparations, diuretics, antispasmodics, uterine relaxants, antiobesity drugs, anabolic drugs, erythropoietic drugs, antiasthmatics, cough suppressants (anti-tussives), mucolytics, anti-uricemic drugs, and the like.

Mixtures of the drugs and medicaments may also be used.

Particular unpleasant tasting drugs include pyridonecarboxylic acid antibacterial agents whose degree of unpleasantness is said to be strongest, such as 5-amino-1-cyclopropyl- 6,8-difluoro-7-(cis-3,5-dimethyl-1-piperazinyl)- 1,4-dihydro-4-(oxoquinoline-3-carboxylic acid, Enoxacin, Pipemidic acid, Ciprofloxacin, Ofloxacin, and Pefloxacin; antiepileptic drugs such as Zonisamide; macrolide antibiotics such as Erythromycin; beta-lactam antibiotics such as penicillins or cephalosporins; psychotropic drugs such as Chlorpromazine; drugs such as Sulpyrine; and antiulcer drugs such as Cimetidine. Suitable among these drugs are pyridonecarboxylic acid antibacterial agents, especially 5-amino-1-cyclopropyl-6,8-difluoro-7-(cis- 3,5-dimethyl-1-piperazinyl)-1,4-dihydro-4-oxoquinoline-3-carboxylic acid or Enoxacin, because the preparations of this invention have an excellent effect of masking the unpleasant taste. An exemplary decongestant is pseudoephedrine hydrochloride and mineral would be zinc salts.

The drugs were used in amounts that are therapeutically effective. While the effective amount of a drug will depend on the drug used, amounts of drug from about 5% to about 65% have been easily incorporated into the present matrix while achieving bitter taste masking. Amounts above about 65% may result in the loss of tasteless properties.

As indicated above, the tastemasked systems may be formed in a variety of ways, such as casting or spray congealing melt dispersions and/or solutions of active in a molten blend of materials. In this way, the tastemasked systems are dispersed in melt hardening and body fluid dispersable/dissolvable materials to form a suspension. The suspensions may then be further formulated with excipient materials to form the final dosage form or material to be used in the final dosage form.

The spatially oriented matrix used to mask the unpleasant taste of the active material must contain two separate components; a major amount of a wax core material having a melting point within the range of about 50° C. to about 200° C. and a separate minor amount of a hydrophobic polymer material.

The wax core material is present in the matrix in amounts of about 10% to about 95% and preferably about 15% to about 85% by weight of the matrix. The wax core material is always present in amounts greater than the hydrophobic polymer and thus has been described as being present in a major amount. The term "core" is used herein to define the substance forming the backbone component of the matrix.

The wax core material may be chosen from a wide variety of materials. Particularly preferred materials are selected from the group consisting of long chain fatty hydrocarbons, esters, acids and alcohols of straight or branched chain alkyls having from 12 to 32 carbon atoms.

Particularly preferred materials are selected from animal waxes, vegetable waxes, petroleum waxes, synthetic waxes, and mixtures thereof and include without limitation beeswax, lanolin, stearic acid, candelilla wax, carnauba wax, microcrystalline wax, carbowax and mixtures thereof.

The hydrophobic polymer material is present in the matrix in amounts of about 1% to about 50% and preferably about 3% to about 10% by weight of the matrix. As discussed above, the hydrophobic polymer is present in amounts less than the wax core material. The hydrophobic polymer material is preferably a material that has some solubility in the wax core material and is selected from a variety of natural polymers or derivative thereof as well as synthetic polymers. Exemplary natural polymers include cellulose, cellulose acetate, cellulose phthalate, methyl cellulose, ethyl cellulose, zein, pharmaceutical glaze, shellac, chitan, pectin, polypeptides, acid and base addition salts thereof, and mixtures thereof. Exemplary synthetic polymers include polyacrylates, polymethacrylates, polyvinyl acetate, acetate phthalate, polyanhydrides, poly(2-hydroxyethyl methacrylate), polyvinylalcohols, polydimethyl siloxone, silicone elastomers, acid and base addition salts thereof, and mixtures thereof. The term "hydrophobic polymer" as used herein refers to polymeric materials that are typically antagonistic to water, i.e., incapable of dissolving in water even though they may have regional areas in the molecule that have some hydrophilic properties.

In addition to the wax core material and the hydrophobic polymer material, the matrix may contain additional ingredients herein referred to as excipients or additives. Exemplary excipients include, but are not limited to sweetening agents, colorants, surfactants, flavors, fragrances, pH modifiers, bulking agents, and mixtures thereof which components may be used in an amount of about 0.01% to about 75% by weight of the matrix.

When preparing the matrix, it is important to consider the physical properties of the materials used. Those compounds which exhibit an elasticity or plastic property appear to be best suited for the matrix, as opposed to very hard waxes such as carnauba. Through a matrix composed completely of a hard natural wax does not give the desired effect, hard natural wax can be used in a portion of the matrix. Portions of the matrix may contain common triglyceride fats and or waxes of a brittle nature such as carnauba to modify physical characteristics of the final matrix. This modification may be necessary to satisfy processing criteria at the congealing phase of the product, or further processing such as tableting or dry powder packaging.

It is believed that dissolution of appropriate polymers in the wax melt formulations modifies the Gibbs Free Energy of the resulting spatially oriented continuum (SOC). The presence of the hydrophobic polymer aids the hydrophobization of the active material immersed in the melt wax by virtue of selective adsorption onto active surface centers.

Spreading of a SOC on a solid substrate is described by the "spreading coefficient" which is a function of the changes of the chemical potentials of the materials involved. Particularly, low-melting solids, such as organic polymers, waxes, and covalent compounds, in general have surface free energies ranging from 100 to 25 ergs/cm$^2$. In the case of a solid substrate, the surface and interfacial tensions are measured individually by contact angle of the wetting liquid on the substrate. For spontaneous wetting this angle should be zero. For the system which involves immersional wetting, the contact angle requirement is less stringent and only requires the contact angle to be less than 90 degrees for immersional wetting to be spontanegus.

Several variables may effect the release characteristics of the dispersed phase and include, particle size, particle size distribution and distribution of the active, material concentration, cooling or solidification rates and conditions, and final form of the system, such as cast sheets or congealed particles.

It is believed that the release mechanism of active components may be a combination of several phenomena. Enzymatic degradation of the matrix, diffusion of the drug through the SOC, competitive adsorption, desorption of hydrophobic components from hydrophilic surface centers, convection of the drug through mesopores and macropores, diffusion of the external medium into the matrix by way of solubility or capillary action through porous structures created by the addition of hydrophilic polymers or water-soluble solids, diffusion from the surface of a capsule due to incomplete coating of drug particles, cracks caused for instance by the difference in thermal expansion between coated drug and matrix, disintegration or erosion of the SOC.

The tasteless pharmaceutical delivery system is prepared by first selecting the matrix components for the particular active ingredient and end use of material. The wax component is melted, and the selected hydrophobic polymer material dissolved in the melt. The composition of hydrophobic polymer material in this system ranges from about 1% to about 50% relative to the selected wax, with preferred levels from about 3% to about 10% by weight of the matrix. Temperatures are adjusted to facilitate the solution, ranging from 50° C. to 200° C., with preferred temperatures from 70° C. to 160° C. Once the hydrophobic polymer material is incorporated satisfactorily, additional wax components can be added and processed to obtain a uniformblend. The composition of additional wax components may varywidely from 0% to 99% relative to the total content of the final matrix but are preferably from 4% to 75% by weight of the matrix. The active ingredients are then added to form the final mixture, which can also be obtained by adding the active ingredients prior to the additional matrix components. It may be necessary at this point to adjust the temperature of the melt to prevent decomposition of the active ingredient.

Slurring of the active ingredient can initially be done by simple stirring. However, in most cases it is necessary to use a high speed mixer and sometimes a colloid mill to obtain a smooth suspension, free of agglomerates. Once a smooth suspension is obtained, it may be necessary to readjust the temperature to provide the proper rheological characteristics for processing, preferably from about 70° C. to about 110° C. The slurry is congealed using technology well knownto the ordinary skilled artisan or rapidly cooled and ground, if required. The final activity of the resultant product may range from 1% to 60%, preferably from 10% to 50%. These final systems and combination of materials result in product with unanticipated benefits of tastemasking noxious drug substances.

In a particularly preferred procedure, a process for preparing a substantially tasteless pharmaceutical delivery system comprises: a) melting a wax core material and a hydrophobic polymer material at a temperature from about 50° C. to about 200° C. to form a matrix; b) blending the matrix to form a homogenous mixture of components; c) adding the active material to the matrix, wherein the temperature of the matrix is maintained below the decomposition temperature of the active material; d) uniformly dispersing the active material within the matrix to obtain of smooth suspension; e) solidifying the mass while spray or spin congealing the molten material to form particles of the substantially tasteless pharmaceutical delivery system. The particles obtained are usually between about 10 μ to about 400 μ in size. Larger particles may be ground if required for further processing.

Since tastemasking is a key feature of the invention, the use of the invention in sublingual or buccal systems is contemplated, but not generally preferred. However, other systems in which the product would not normally be expected to be retained in the mouth for significant amounts of time are contemplated. Thus, chewable and/or dissolvable dosage forms would be particularly improved with this technology. Further, fluid oral dosage forms would also be particularly improved with this technology.

One dosage form contemplated, involves the use of gelatin or other plastic matrix(es) in a capsule containing the inventive aggregate and/or materials containing the inventive delivery system in combination with one or more conventional excipients.

The term "excipients" as used herein mean substances and materials generally used in the drug or food industry which do not alter the character and function of the active component of the aggregate.

Flavors which may optionally be added to the delivery system are those well known in the confectionery art. For example, synthetic flavor oils, and/or oils from plants, leaves, flowers, fruits and so forth, and combinations thereof are useful.

Representative flavor oils include spearmint oil, peppermint oil, cinnamon oil, and oil of wintergreen (methylsalicylate). Also useful are artificial, natural or synthetic fruit flavors such as citrus oils including lemon, orange, grape, lime, and grapefruit, and fruit essences including apple, strawberry, cherry, pineapple and so forth.

The amount of flavoring agent employed is normally a matter of preference subject to such factors as flavor type, base type and strength desired. In general, amounts of about 0.05% to about 5.0% by weight of the final product are useful with amounts of about 0.3% to about 1.5% being preferred and about 0.8% to about 1.2% being most preferred.

The matrix may contain a sweetening agent. Sweetening agents may be selected from a wide range of materials such as water-soluble sweetening agents, water-soluble artificial sweeteners, and dipeptide based sweeteners, including mixtures thereof. Without being limited to particular sweeteners, representative illustrations encompass:

A. Water-soluble sweetening agents such as monosaccharides, disaccharides and polysaccharides such as xylose, ribose, glucose, mannose, galactose, fructose, dextrose, sucrose, sugar, maltose, partially hydrolyzed starch, or corn syrup solids and sugar alcohols such as sorbitol, xylitol, mannitol and mixtures thereof.

B. Water-soluble artificial sweeteners such as the soluble saccharin salts, i.e., sodium or calcium saccharin salts, cyclamate salts, acesulfam-K and the like, and the free acid form of saccharin.

C. Dipeptide based sweeteners such as L-aspartyl L-phenylalanine methyl ester and materials described in U.S. Pat. No. 3,492,131 and the like.

While delivery systems based on the instant invention are generally solid or semi-solid, it is contemplated that they may be employed, with or without the conventional supplemental agents, as principal components of systems to be dissolved or dispersed in water or other ingestible liquids for ingestion in a drinkable form.

The excipients are added to the matrix anytime during processing. It should be recognized that certain excipients should be added prior to, during or after the active material is blended into the matrix in order to achieve uniform distinction of the ingredients. Preferably, excipients in liquid form are added before the active material whereas powdered excipients may be added before or after the active material is added.

The following examples are illustrative of preferred embodiments of the invention and are not to be construed as limiting the invention thereto. All percentages are based on the percent by weight of the matrix unless otherwise indicated and all totals equal 100% by weight.

EXAMPLE 1

This example demonstrates the production of tasteless granules of pseudoephedrine hydrochloride.

To a suspension of beeswax (81.6% w/w) and ethyl cellulose (10 cps, 3% w/w) which was melted at a temperature of 70°–80° C. and blended to form a homogenous mixture was added pseudoephedrine hydrochloride (15.4% w/w). The suspension was blended for 10–15 minutes, and cooled in air while spin congealing to form a solid particulate material. Particles of spin congealed material when chewed by a panel comprising at least five members, the product did not exhibit any bitter taste.

EXAMPLE 2

This example demonstrates the production of various forms of active material.

To a molten blend of beeswax, carnauba wax or Witepsol® (a triglyceride fat of Hüls America Inc.) each at (82% w/w) and ethyl cellulose (10 cps, 3% w/w) which were melted, blended and maintained at a temperature of 120° C. was added pseudoephedrine hydrochloride (15% w/w).

The slabs produced that were based on carnauba wax and Witepsol® when chewed exhibited a bitter taste, while granules and slabs based on beeswax when chewed did not exhibit a bitter taste. Therefore, the mechanism of congealing and geometry of the system influence the degree of taste.

COMPARATIVE EXAMPLE A

This example demonstrates the production of comparative granules with beeswax alone.

The procedure of Example 1 was repeated with melted beeswax (85% w/w) blended with pseudoephedrine hydrochloride (15% w/w).

The granules when chewed exhibited a bitter taste. Therefore the presence of the hydrophobic polymer material is required to create a tastemasked system.

EXAMPLE 3

This example demonstrates the preparation of a delivery system with a hydrophobic polymer material.

The procedure of Example 1 was repeated using a blend of beeswax (82% w/w) with ethyl cellulose (10 cps 3% w/w) or a methylacrylate polymer (Eudragit® RS100 by Rohm Pharma) (3% w/w). The material was cast into a block and taste tested. Neither of the systems exhibited a bitter taste when tested. It is therefore concluded that the hydrophobic polymer material properties such as hydrophobicity and miscibility in the core wax material influence the tastemasking properties of the matrix.

EXAMPLE 4

The procedure of Example 1 was repeated to prepare granulars from 6-methoxy erythromycin A (8%, 16% and 25% w/w respectively) suspended in a blend of ethyl cellulose, Ethocel (10 cps., 3% w/w), in beeswax (89% and 72% w/w, respectively). The granulars when chewed did not exhibit a bitter taste. Therefore, these systems are applicable to alternative drug forms.

EXAMPLE 5

The procedure of Example 1 was repeated to prepare: granulars from acetaminophen (35.38% w/w), pseudoephedrine hydrochloride (3.32% w/w), chloropheniramine maleate (0.21% w/w) and dextromethorphan (1.10% w/w) suspended in a blend of ethyl cellulose, Ethocel (10 cps, 3.00% w/w), beeswax (17.00% w/w), sorbitan monoloeate, 3.00% w/w and mono- and di-glycerides, 36.99% w/w. The granulars when chewed did not exhibit a bitter taste. Therefore, these systems are applicable to wax mixtures.

EXAMPLE 6

The procedure of Example 1 was repeated to prepare granulars from ascorbic acid (19.84% w/w) and folic acid (0.16% w/w) suspended in a blend of ethyl cellulose, (10 cps., 4.00% w/w) sorbitan monoloeate (4.00% w/w), hydrogenated vegetable oil, (8.00% w/w) and candelilla wax (64.00% w/w). The particle granulars when chewed did not exhibit a sour taste. Therefore, these systems are applicable to wax mixtures and other wax materials.

EXAMPLE 7

The procedure of Example 1 was repeated to prepare granulars from ibuprofen (40.00% w/w) suspended in a blend of ethyl cellulose, (10 cps., 3.00%w/w), sorbitan monoleate (3.00% w/w), beeswax (12.25% w/w) carnauba wax (6.00% w/w) and mono- and di- glycerides (35.75% w/w). The granulars when chewed did not exhibit a bitter taste. Therefore, these systems are applicable to wax mixtures.

The invention being thus described, it will be obvious that the same may be varied in many ways. Such variations are not be regarded as a departure from the spirit and scope of the invention and all such modifications are intended to be included within the scope of the following claims.

What is claimed is:

1. A substantially tasteless pharmaceutical delivery system, which comprises a molten blend of:
   a) an active material; and
   b) a spatially oriented matrix comprising:
      (i) a major amount of about 10% to about 95% by weight of the matrix of a wax core material having a melting point within the range of about 50° C. and about 200° C.; and
      (ii) a minor amount of about 1% to about 50% by weight of the matrix of a hydrophobic polymer material selected from the group consisting of natural polymers and synthetic polymers,
   wherein the total amount of the matrix is equal to 100%.

2. The delivery system of claim 1, wherein the active material is a pharmaceutical drug.

3. The delivery system of claim 1, wherein the active material is selected from the group consisting of analgesics, anti-inflammatories, antihistamines, antitussives, expectorants, decongestants, narcotics, antibiotics, bronchodilators, cardiovasculars, central nervous system drugs, minerals, vitamins,-metal salts, and mixtures thereof.

4. The delivery system of claim 1, wherein the wax core material is selected from the group consisting of long chain fatty hydrocarbons, esters, acids and alcohols of straight or branched chain alkyls having from 12 to 32 carbon atoms.

5. The delivery system of claim 4, wherein the wax core material is selected from the group consisting of animal waxes, vegetable waxes, petroleum waxes, synthetic waxes, and mixtures thereof.

6. The delivery system of claim 5, wherein the wax core material is selected from the group consisting of beeswax, lanolin, stearic acid, candelilla wax, carnauba wax, microcrystalline wax, carbowax and mixtures thereof.

7. The delivery system of claim 1, wherein the hydrophobic polymer material is present in an amount of about 1% to about 50% by weight of the matrix.

8. The delivery system of claim 1, wherein the hydrophobic polymer material is present in an amount of about 3% to about 10% by weight of the matrix.

9. The delivery system of claim 1, wherein the natural polymer is selected from the group consisting of cellulose, cellulose acetate, cellulose phthalate, methyl cellulose, ethyl cellulose, zein, pharmaceutical glaze, shellac, chitan, pectin, polypeptides, acid and base addition salts thereof, and mixtures thereof.

10. The delivery system of claim 1, wherein the synthetic polymer-is selected from the group consisting of polyacrylates, polymethacrylates, polyvinyl acetate, polyvinyl acetate phthalate, polyanhydrides, poly(2-hydroxyethyl methacrylate), polyvinylalcohols, polydimethyl siloxone, silicone elastomers, acid and base addition salts thereof, and mixtures thereof.

11. The delivery system of claim 1, wherein the matrix includes an excipient.

12. The delivery system of claim 1, wherein the excipient is present in the matrix in an amount of about 0.01% to about 75% by weight of the matrix.

13. The delivery system of claim 1, wherein the excipient is selected from the group consisting of sweetening agents, colorants, surfactants, flavors, fragrances, pH modifiers, bulking agents, and mixtures thereof.

14. A substantially tasteless pharmaceutical delivery system which comprises:
   a) an effective amount of an active material selected from the group consisting of analgesics, anti-inflammatories, antihistamines, antitussives, expectorants, decongestants, narcotics, antibiotics, bronchodilators, cardiovasculars, central nervous system drugs, minerals, vitamins, metal salts, and mixtures thereof; and
   b) a spatially oriented matrix comprising:
      (i) from about 10% to about 95% of a wax core material having a melting point within the range of about 50° C. and about 200° C.; and
      (ii) from about 1% to about 50% of a hydrophobic polymer material; and remaining amount up to 100% of an additional excipient.

* * * * *

UNITED STATES PATENT AND TRADEMARK OFFICE
CERTIFICATE OF CORRECTION

PATENT NO. : 5,494,681
DATED : February 27, 1996
INVENTOR(S) : CUCA et al.

It is certified that error appears in the above-indentified patent and that said Letters Patent is hereby corrected as shown below:

Claim 3, column 9, line 48, change "vitamins,-metal" to —vitamins, metal—;

Claim 10, column 10, line 21, change "polymer-is" to —polymer is—;

column 5, line 42, change "spontanegus" to —spontaneous—; and column 6, line 9, change "uniformblend" to —uniform blend—.

Signed and Sealed this

Eleventh Day of June, 1996

*Attest:*

BRUCE LEHMAN

*Attesting Officer*     *Commissioner of Patents and Trademarks*